United States Patent [19]

Mitsugi et al.

[11] 4,016,037
[45] Apr. 5, 1977

[54] METHOD FOR PRODUCING L-AMINO ACID

[75] Inventors: Koji Mitsugi, Yokohama; Konosuke Sano, Machida; Kenzo Yokozeki, Kawasaki; Kazuhiko Yamada, Fujisawa; Ichiro Noda, Yokohama; Teruhiko Kagawa; Chikahiko Eguchi, both of Kawasaki; Naohiko Yasuda, Yokosuka; Fumihide Tamura, Kawasaki; Kazushi Togo, Yokohama, all of Japan

[73] Assignee: Ajinomoto Co., Inc., Tokyo, Japan
[22] Filed: Oct. 15, 1975
[21] Appl. No.: 622,519
[52] U.S. Cl. .................................................. 195/29
[51] Int. Cl.$^2$ ........................................ C12D 13/06
[58] Field of Search ...................................... 195/29

[56] References Cited
UNITED STATES PATENTS

| | | | |
|---|---|---|---|
| 3,320,135 | 5/1967 | Okumura et al. | 195/29 |
| 3,494,831 | 2/1970 | Nakayama et al. | 195/29 |

*Primary Examiner*—Alvin E. Tanenholtz
*Attorney, Agent, or Firm*—Cooper, Dunham, Clark, Griffin & Moran

[57] ABSTRACT

L-amino acids are produced by fermenting a hydantoin compound with *Flavobacterium aminogenes* or its enzymes.

14 Claims, No Drawings

METHOD FOR PRODUCING L-AMINO ACID

This invention relates to a method for producing L-amino acid, and particularly relates to a method for producing L-phenylalanine, L-tryptophane and their derivatives from 5-benzylhydantoin, 5-indolylmethylhydantoin and their derivatives.

The hydantoin compounds as mentioned above are produced by Strecker's reaction from aldehyde, and are intermediates for producing L-amino acids. For example, the hydantoin compounds are hydrolyzed to L-amino acids with the enzymes produced by *Flavobacterium proteus* ATCC 12848 (Japanese Patent Publication No. 13850/1967).

It has now been found that a newly *Flavobacterium aminogenes* produces mainly in its cells emzyme having remarkably high activity for converting hydantoin compounds of formula I

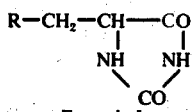

Formula I (R is phenyl or substituted phenyl radicals or indolyl or substituted indolyl radicals)

to L-amino acids of formula II, and that

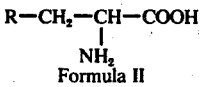

Formula II (R is the same as in formula I)

the L-amino acids are produced in very high yield, when the hydantoin compounds are held in aqueous solution in the presence of the enzyme of *Flavobacterium aminogenes* nov. sp.

Taxonomic characteristics of *Flavobacterium aminogenes* nov. sp. AJ-3912 (FERM-P 3133).

1. Morphological characteristics; rods, 0.3 – 0.5 × 0.7 – 0.9 micron, non pleomorphic, non-motile, gram negative, non-spore forming and non-acidfast.

2. Cultural characteristics;
Nutrient agar colonies; poor growth, circular, convex or raised, entire and straw yellow.
Agar stroke; moderate growth, smooth, filiform, amber, glistning transluscent
Nutrient broth; moderate growth, turbid, non-growth on surface, viscoid sediment.
Geratin stab; stratiform liquefaction.
Litmus milk; unchanged.
BCP milk; slightly acidified, no-liquefaction.

3. Physiological characteristics;
nitrites produced from nitrates, denitrofication not observed, indol not produced, MR test-negative, VP test-negative, $H_2S$ produced, starch not hydrolyzed, citric acid not utilized in Koser's medium, but utilized in Christensen medium, nitrates and ammonia not utilized, water soluble pigment not produced, urease-negative, oxydase-slightly positive, catalase-positive, growth at PH 6–9, maximum growth temperature 34° C, aerobic, OF-test oxydative, acid but no gas from D-glucose and no acid and no gas from L-arabinose, D-xylose, D-mannose, D-fructose, D-galactose, maltose, lactose, trehalose, D-sorbitol, D-mannitol, D-inositol, glycerol, starch, D-ribose, L-rhamnose, L-raffinose, eryithritol, erithritol, dulcitol, cellobiose, melibiose, adonitol, salicin and esculin.

Assimilated acetic acid, lactic acid D-glucose, D-xylose, D-mannitol and protocatecuic acid, but not assimilated p-hydroxy-benzoic acid, gluconic acid and lactose.

Casein-hydrolyzed, DNA ase-positive, grown on 2% NaCl but not 5%, DNA base composition 69.0%GC.

According to Bergey's Manual of Determinative Bacteriology 8 th Ed. (1974), Strain AJ 3912 belongs to the genus *Flavobacterium* since it is gram-negative rods, non-motile, aerobic, oxidase-positive (week), catalase-positive, yellow chromogenesis, and glucose is slowly decomposed only oxidatively.

Flavobacterium species are divided into two section, first section has 26–43% GC-content in DNA (Section I) and second section has 63–70% GC-content (section II). Strain 3912 belongs to section II since it has 69% GC-content. Four motile species and two non-motile species are belongs to Section II.

Strain AJ 3912 is non-motile, however, it is different from *F. capsulatum* in the following points, that is, *F. capsulatum* is halophilic, does not liquefy gelatin, and does not produce acid from lactose, sucrose, maltose, xylose, sorbitol, and raffinose. Strain AJ 3912 is also different from *F. lutescens* in the following points; *F. lutescens* is halophilic, grows at 37° C, and hydrolyze starch but strain AJ 3912 is not halophilic, does not grow at 37° C, and does not hydrolyse starch.

For these reasons, it is recognized that Strain AJ 3912 is a novel species of the genus Flavobacterium.

When *Flavobacterium aminogenes* nov. sp. is cultured in conventional media, the enzyme of converting the hydantoin compounds to L-amino acid is produced mainly in the cells and slightly in the culture broth. The culture media used contain carbon source, nitrogen source, inorganic ions, and where required organic nutrients. When culture media containe the hydantoin compound of formula I such as 5-indolymethyl-hydantoin, the enzyme activity is generally much higher.

Carbon source are, for example, carbohydrates such as glucose, xylose, sucrose, starch hydrolyzate, starch, or molasses, organic acids such as acetic acid or lactic acid, alcohols such as ethylalcohol, methylalchol, or glycerol.

Nitrogen source are, for example, ammonia, nitrogen ions, and urea. Inorganic ions are, for example, phosphate, magnesium, ferrous, calcium, potassium, maganese and other conventional ones. Minor organic nutrients are, for example, vitamines, amino acids, and crude materials containing those minor organic nutrients such as yeast extract, peptone, bouillon, corn steep liquor, or casein hydrolysate.

Cultivation is carried out at pH 6 to 9 and preferably 20° to 40° C under aerobic conditions. After 1 to 5 days cultivation, the enzyme are produced in the cells.

As the enzyme source, culture broth containing intact cells, homogenates of cells, sonicates of cells, freeze-dried cells, or cells dried with solvents and the like are preferably used. Protein fractions separated, for example, from the homogenate of cells, or the sonicate of cells by conventional methods such as gel-filtration or salting-out method can be also used as the enzyme source. It is therorized that a number of enzymes participate in the reaction of converting the hydantoin compounds to L-amino.

Hydantoin compounds of this invention are, for example, 5-benzyl-hydantoin
5-(4'-hydroxybenzyl)-hydantoin
5-(3',4'-dihydroxybenzyl)-hydantoin
5-(2',4'-dihydroxybenzyl)-hydantoin
5-(3',4'-methylenedioxybenzyl)-hydantoin
5-(3',4'-dimethoxybenzyl)-hydantoin
5-(3'(4')-methoxy-4'(3')-hydroxybenzyl)-hydantoin
5-(3',4'-isopropylidenedioxybenzyl)-hydantoin
5-(3',4'-cyclohexylidenedioxybenzyl)-hydantoin
5-inodolylmethyl-hydantoin
5-(5'-hydroxy-indolymethyl)-hydantoin
5-(5'-methyl-indolymethyl)-hydantoin and
5-(3',4',5'-trihydroxybenzyl)-hydantoin The following L-amino acids are produced from the corresponding hydantoin compounds;

phenylalanine
tyrosine
3,4-dihydroxyphenylalanine
2,4-dihydroxyphenylalanine
3,4-methylenedioxyphenylalanine
3,4-dimethoxyphenylalanine
3(4)-methoxy-4(3)-hydroxyphenylalanine
3,4-isoropylidendioxyphenylalanine
3,4-cyclohexylidenedioxyphenylalanine
tryptophane
5-hydroxytryptophane
5-methyltryptophane and
3,4,5-trihydroxyphenylalanine The reaction mixtures contain the hydantoin compound and the enzyme or the enzyme source of *Flavobacterium aminogenes* nov. sp. The amounts of hydantoin compounds in the reaction mixture are usually less than 50g/dl, and preferably less than 10g/dl. Usually water is used as the solvent. Hydrophilic or hydrophobic organic solvents are used with water in order to increase the solubility of the hydantoin compounds.

Particularly, in the formation of L-tryptophane from 5-indolymethyl hydantoin, it is better to add the agents as follows in the reaction mixture to prevent further decomposition of L-tryplophane. NaCN, NH$_2$OH·HCl, phenylhydrazine·HCl, semicarbazide·HCl, potassium ferricyanide, D-cycloserine, sodium azide and phenol and so on.

In the reaction mixture containing 5-dihydroxybenzyl-hydantoin, 5-trihydroxylbenzyl-hydantoin, and 5-(5'-hydroxyindolymethyl)-hydantoin, reducing agents such as sodium sulfite are added to prevent the oxidation of the hydantoin compounds.

The reaction mixture is maintained at pH 5 to 11 and preferably 7 to 10, and at 15° to 70° C and preferably 30° to 50° C.

After 5 to 150 hours, L-amino acid is accumulated in the reaction mixture. The accumulated L-amino acid can be recovered by conventional means such as ion chromatography.

EXAMPLE 1

An aqueous culture medium was prepared to contain 0.5 g/dl glucose, 1.0 g/dl yeast extract, 1.0 g/dl peptone, 0.5 g/dl NaCl, and 0.2 g/dl DL-5-indolymethyl hydantoin. Fifty Ml batches of the aqueous culture medium were placed in 500 ml shaking flasks, heated with steam, and inoculated with *Flavobacterium aminogenes* nov. sp. AJ 3912. Each flask was shaken at 30° C for 16 hours.

Cells were separated from 500 ml of culture broth by centrifuging, washed with physiological saline, and suspended in 500 ml of 0.1 M phosphate-buffer (pH 8.0).

Each 5 ml of the suspension was added with 50 mg of the hydantoin compounds listed in Table 1 and 15 mg of sodium sulfite in the cases of DL-5-(3',4'-dihydroxybenzyl)-hydantoin, and D-5-(5'-hydroxyindolymethyl)-hydantoin, and held at 37° C for 24 hours.

The amount of L-amino acid shown in Table 1 was accumulated in the reaction mixture.

Table 1

| Hydantoin compound | L-Amino acid accumulated | (mg/ml) |
|---|---|---|
| DL-5-benzyl-hydantoin | L-phenylalanine | 8.7 |
| DL-5-(3',4'-dihydroxybenzyl)-hydantoin | L-3,4-dihydroxyphenyl-alanine | 8.9 |
| DL-5-(3',4'-methylenedioxy-benzyl)-hydantoin | L-3,4-methylenedioxy-phenylalanine | 9.0 |
| DL-5-(3',4'-dimethoxybenzyl)-hydantoin | L-3,4-dimethoxy-phenylalanine | 0.5 |
| DL-5-(3'-methoxy-4'-hydroxy-benzyl)-hydantoin | L-3-methoxy-4-hydroxy-phenylalanine | 8.7 |
| DL-5-indolymethyl-hydantoin | L-tryptophane | 2.6 |
| DL-5-(5'-hydroxyindolymethyl)-hydantoin | L-5-hydroxytryptophane | 0.72 |
| D-5-(5'-hydroxyindolymethyl)-hydantoin | L-5-hydroxytryptophane | 0.73 |

EXAMPLE 2

*Flavobacterium aminogenes* AJ 3912 was exposed to N-nitro-N'-methyl-N-nitrosoguanidine and two mutants, AJ 3939 (FERM-P 3134) and AJ 3940 (FERM-P 3135), which are incapable of growing in a medium containing L-tryptophan as a sole nitrogen source are isolated from the exposed parent strains by replication method.

AJ 3912, AJ 3939 and AJ 3940 were cultured in 3 ml of the following Medium I and Medium II placed in 30 ml test tube, at 30° C for 24 hours.

Table 2

|  | Medium I | Medium II |
|---|---|---|
| glucose | 5 g/l | 5 g/l |
| KH$_2$PO$_4$ | 1 g/l | 1 g/l |

Table 2-continued

| | Medium I | Medium II |
|---|---|---|
| $K_2HPO_4$ | 3 g/l | 3 g/l |
| $MgSO_4 \cdot 7H_2O$ | 0.1 g/l | 0.1 g/l |
| $MgCl_2$ | 10 mg/l | 10 mg/l |
| $CaCl_2 \cdot 2H_2O$ | 1 mg/l | 1 mg/l |
| metal ions solution* | 1 ml/l | 1 ml/l |
| $(NH_4)_2SO_4$ | 1.5 g/l | — |
| urea | 1.5 g/l | — |
| L-tryptophane | — | 7.3 g/l |

*Metal ions solution: 8800 mg $ZnSO_4 \cdot 7H_2O$, 970 mg $FeCl_3 \cdot 6H_2O$, 393 mg $CuSO_4 \cdot 5H_2O$, 72 mg $MnCl_2 \cdot 4H_2O$, 37 mg $(NH_4)_6MO_7O_{24} \cdot 4H_2O$, and 88 mg $NaB_4O_7 \cdot H_2O$ were contained in 1 liter water.

Growth was determined by measuring optical density at 562nm of the culture broth. The results are shown in Table 3.

Table 3

| Strain | Relative growth | |
|---|---|---|
| | Medium I | Medium II |
| AJ 3912 | 100 | 100 |
| AJ 3939 | 98.6 | 10.1 |
| AJ 3940 | 100 | 12.6 |

Cells of AJ 3939 and AJ 3940 were obtained by the same manner as in Example 1, and conversion reaction was carried out by the same manner as in Example 1. AJ 3939 and AJ 3940 produced 5.4 mg/ml and 5.6 mg/ml L-tryptophane, respectively.

EXAMPLE 3

*Flavobacterium aminogenes* AJ 3940 was cultured in the same manner as in Example 1, and the resultant culture broth was centrifuged to separate cells. The cells were washed with physiological saline.

Ten of the cells was suspended in 200 ml 0.1 M phosphate buffer solution (pH 8.0) which contained 2g DL-5-indolylmethylhydantoin. The reaction mixture was held at 43° C for 27 hours. The reaction mixture contained 1.75g L-tryptophan.

The reaction mixture was centrifuged to remove cells, filtered with ultra-filtering membrane and evaporated to 30 ml. Crystals were obtained by cooling, and recrystallized in water-ethanol solution. It weighed 1.30 g.

The crystals were identified with authentic L-tryptophane in NMR spectrum, X-ray diffraction pattern, Rf of paper chromatography and optical rotation. Optical purity of the crystals was 99.1%.

EXAMPLE 4

Cells of *Flavobacterium aminogenes* AJ 3912 were prepared by the same manner as in Example 1.

The cells (50g) were suspended in 1 liter 0.1M phosphate buffer (pH 8.0) containing 3 g sodium sulfite and 10g D-5-(5'-hydroxy indolylmethyl)-hydantoin. The reaction mixture was held at 37° C for 24 hours, and contained 0.73 g L-5-hydroxytryptophan. L-5-Hydroxytryptophane crystals (0.53g) were obtained by the analogous manner to that in Example 3.

The crystals were identified with authentic L-5-hydroxy tryptophane by analogous manner described in Example 3. Optical purity of the crystals was 99.2%.

EXAMPLE 5

In the same manner as in Example 4, DL-benzyl-hydantoin was used in place of D-5-(5'-hydroxy indolymethyl)-hydantoin.

The reaction mixture contained 1.73 g L-phenylalanine. Crystals (1.41g) were obtained by the same manner as in Example 3.

The crystals were identified with L-phenylalanine in NMR spectrum, X-ray diffraction, Rf of paper chromatography, and optical rotation. The optical purity was 98.4%.

EXAMPLE 6

An aqueous culture medium was prepared to contain, per deciliter, 0.5 g glucose, 0.5 g $(NH_4)_2SO_4$, 0.1g $KH_2PO_4$, 0.3g $K_2HPO_4$, 0.01g $MgSO_4 \cdot 7H_2O$, 0.001g $CaCl_2 \cdot 2H_2O$, 5 ml corn steep liquor, adjusted to pH 7.0 and 50 ml batch of the medium was placed in 500 ml flasks.

After sterilizing at 120° C for 15 minutes, the medium was inoculated with AJ 3940, and held at 30° C for 12 hours with shaking.

The same medium as mentioned above was added additionally with 0.35 g/dl DL-5-indolylmethylhydantoin, and inoculated with 2.5 ml of the culture broth mentioned above, and held at 30° C for 20 hours with shaking.

The culture broth (5 ml) was added with 250 mg of each hydantoin compounds listed in Table 4, and held at 40° C for 90 hours. In the case of 5-(5'-hydroxyindolymethyl)-hydantoin and 5-(3',4'-dihydroxybenzyl)-hydantoin, the suspension was further added with 15 mg sodium sulfite. The amounts of L-amino acids shown in Table 4 were found in the reaction mixture.

Table 4

| Hydantoin compound | L-Amino acid accumulated | mg/ml |
|---|---|---|
| DL-5-(3',4'-dihydroxybenzyl)-hydantoin | L-3,4-dihydroxy-phenylalanine | 27.0 |
| DL-5-(3',4'-methylenedioxybenzyl)-hydantoin | L-3,4-methylenedioxy-phenylalanine | 44.5 |
| DL-5-(3',4'-dimethoxybenzyl)-hydantoin | L-3,4-dimethoxybenzyl-phenylalanine | 3.1 |
| DL-5-(3'-methoxy-4'-hydroxybenzyl)-hydantoin | L-3-methoxy-4-hydroxy-phenylalanine | 12.4 |
| DL-5-benzyl-hydantoin | L-phenylalanine | 42.6 |
| DL-5-(5'-hydroxyindorylmethyl)-hydantoin | L-5-hydroxytryptophane | 8.9 |

EXAMPLE 7

The cells suspension described in Example 6 was added with 250 mg DL-5-indolylmethyl-hydantoin, 290 mg inosine and 50 mg $KH_2PO_4$, adjusted to pH 8.1, and held at 40° C for 110 hours.

L-Tryptophane inosine salts precipitated in the reaction mixture were dissolved by adding to the reaction mixture with 5 ml of 1N NaOH. The reaction mixture contained 44.5 mg/ml L-tryptophane.

EXAMPLE 8

Cells of *Flavobacterium aminogenes* AJ 3912 (15g) prepared by the same manner as the Example 1 were suspended in 300 ml of 0.1M phosphate buffer (pH 8.0). The suspension was added with 3g of 5-(3',4'-methylenedioxybenzyl)-hydantoin, (reaction mixture I), or 3g of 5-(3',4'-dihydroxybenzyl)-hydantoin and 0.9g of sodium sulfite (reaction mixture II), or 3g of 5-(3'-methoxy-4'-hydroxybenzyl)-hydantoin and 0.9g of sodium sulfite (reaction mixture III). The reaction mixtures were held at 37° C for 30 hours, and reaction mixture I contained 2.73g of L-3,4-methylenedioxyphenylalanine, reaction mixture II contained 2.65g of L-3,4-dihydroxyphenylalanine, and reaction mixture III contained 2.78g of L-3-methoxy-4-hydroxyphenylalanine.

By the same manner described in Example 4, 1.54g of L-3,4-methylenedioxyphenylalanine crystals 1.92g of L-3,4-dihydroxyphenylalanine crystals and 1.71g L-3-methoxy-4-hydroxyphenylalanine crystals were recovered.

EXAMPLE 9

In the method as described in Example 1, the reaction mixture contained 25mg DL-5-indolymethyl-hydantoin in place of 50 mg. of the hydantion compound in Table 1, and further contained the additive listed in Table 5. The reaction mixture was held at 37° C for 16 hours.

The amounts of L-tryptophane accumulated in the reaction mixture are shown in Table 5.

Table 5

| Additive | Concentration mm | L-Tryptophan accumulated (mg/ml) |
| --- | --- | --- |
| none | — | 1.93 |
| NH$_2$OH.HCl | 50 | 4.14 |
| phenylhydrazine.HCl | 50 | 4.32 |
| NaCN | 5 | 2.58 |
| semicarbazide.HCl | 5 | 2.48 |
| potassium ferricyanide | 5 | 2.64 |
| D-cycloserine | 5 | 2.59 |
| sodium azide | 50 | 3.33 |
| phenol | 5 | 2.31 |

FERM-P numbers of *Flavobacterium aminogenes* nov. sp. are accession numbers accorded by the Fermentation Research Institute, Agency of Industrial Science and Technology, at Inage, Chiba-shi, Japan. All strains having the FERM-P number are available from the Fermentation Research Institute.

What is claimed is:

1. A method for producing an L-amino acid of the formula:

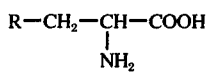

which comprises:
a. holding a hydantoin compound of the formula:

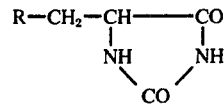

at pH 5 to 11 in an aqueous solution at 15° to 70° C in the presence of an effective amount of enzyme produced by *Flavobacterium aminogenes* until the L-amino acid accumulates in the solution; said enzyme being capable of converting said hydantoin compound to said L-amino acid, and in said formula, R being phenyl or substituted phenyl radicals or indolyl or substituted indolyl radicals; and b. recovering the L-amino acid formed from said aqueous solution.

2. A method as set forth in claim 1, wherein said hydantoin compound is 5-benzylhydantoin.

3. A method as set forth in claim 1, wherein said hydantoin compound is 5-indolylmethyl-hydantoin.

4. A method as set forth in claim 1, wherein said hydantoin compound is 5-(3',4'-dihydroxybenzyl)-hydantoin.

5. A method as set forth in claim 1, wherein said hydantoin compound is 5-(3'(4')- methoxy - 4'(3')-hydroxybenzyl)-hydantoin.

6. A method as set forth in claim 1, wherein said hydantoin compound is 5-(3',4'-methylenedioxybenzyl)-hydantoin.

7. A method as set forth in claim 1, wherein said hydantoin compound is 5-(3',4'-isopropylidene dioxybenzyl)-hydantoin.

8. A method as set forth in claim 1, wherein said hydantoin compound is 5-(5'-hydroxy-indolylmethyl)-hydantoin.

9. A method as set forth in claim 1, wherein said enzyme is produced by a mutant of *Flavobacterium aminogenes* which mutant is incapable of growing in a medium containing L-tryptophan as a sole nitrogen source.

10. A method as set forth in claim 1, wherein said enzyme is produced by *Flavobacterium aminogenes* FERM - P 3133, 3134, or 3135.

11. A method as set forth in claim 1, wherein said enzyme is produced by culturing *Flavobacterium aminogenes* in an aqueous culture medium containing said hydantoin compound.

12. A method as set forth in claim 1, wherein said aqueous solution contains hydroxylamine hydrochloride, phenylhydrozine hydrochloride, sodium cyanide, semicarbazide hydrochloride, potassium ferricyanide, D-cycloserine, sodium azide or phenol.

13. A method as set forth in claim 1, wherein intact cells of *Flavobacterium aminogenes*, homogenates of said cells, sonicates of said cells, or freeze-dried cells of said *Flavobacterium aminogenes* are used as the enzyme source.

14. A method as set forth in claim 1, wherein said hydantoin compound is 5-(3',4'-dimethoxybenzyl)-hydantoin.

* * * * *